United States Patent
Wu

(10) Patent No.: US 9,567,278 B2
(45) Date of Patent: Feb. 14, 2017

(54) PRODUCTION OF PARA-PROPYLBENZALDEHYDE

(71) Applicant: Albemarle Corporation, Baton Rouge, LA (US)

(72) Inventor: Tse-Chong Wu, Baton Rouge, LA (US)

(73) Assignee: ALBEMARLE CORPORATION, Baton Rouge, LA (US)

(*) Notice: Subject to any disclaimer, the term of this patent is extended or adjusted under 35 U.S.C. 154(b) by 0 days.

(21) Appl. No.: 14/762,677

(22) PCT Filed: Mar. 13, 2014

(86) PCT No.: PCT/US2014/026096
§ 371 (c)(1),
(2) Date: Jul. 22, 2015

(87) PCT Pub. No.: WO2014/151608
PCT Pub. Date: Sep. 25, 2014

(65) Prior Publication Data
US 2015/0368175 A1    Dec. 24, 2015

Related U.S. Application Data

(60) Provisional application No. 61/791,393, filed on Mar. 15, 2013.

(51) Int. Cl.
*C07C 45/00* (2006.01)
*C07C 45/49* (2006.01)

(52) U.S. Cl.
CPC ..................... *C07C 45/49* (2013.01)

(58) Field of Classification Search
CPC .................................................. C07C 45/49
USPC ....................................................... 568/428
See application file for complete search history.

(56) References Cited

U.S. PATENT DOCUMENTS

| | | |
|---|---|---|
| 2,485,237 A | 10/1949 | Gresham et al. |
| 4,195,040 A | 3/1980 | Renner |
| 4,368,336 A | 1/1983 | Fujiyama et al. |
| 4,460,794 A | 7/1984 | Fujiyama et al. |
| 4,622,429 A * | 11/1986 | Blank ............... C07C 45/49 568/428 |
| 6,080,892 A | 6/2000 | Scrivens et al. |
| 7,154,008 B2 | 12/2006 | Kato et al. |
| 7,157,510 B2 | 1/2007 | Xie et al. |

FOREIGN PATENT DOCUMENTS

| | | | |
|---|---|---|---|
| CN | 1472185 A | 2/2004 | |
| CN | 1660747 A | 8/2005 | |
| DE | 403489 A | 9/1924 | |
| DE | 2801887 A1 | 6/1979 | |
| EP | 0064690 A1 | 11/1982 | |
| EP | 1524256 A1 * | 4/2005 | ............ C07C 45/49 |

OTHER PUBLICATIONS

ISR; PCT/US2014/026096, Sep. 5, 2014.*
Olah, George A., et al., "Aromatic Substitution XXXIX. Varying Selectivity in Electrophilic Formylation of Toluene and Benzene", Journal of Am. Chem. Soc., 1976, 98:1, pp. 296-297.
Braddley G., and Kenner, J., "The Meta-alkylation of Aromatic Hydrocarbons by the Friedel-Crafts Reaction", J. Chem. Soc., 1935, pp. 303-309.
Crounse, Nathan N., "The Gattermann-Koch Reaction. The Formylation of Isopropylbenzene Under Pressure", J. Am. Chem. Soc., 1949, 71, pp. 1263-1264.
Crounse, Nathan N., "The Gattermann-Koch Reaction", The Hilton-Davis Chemical Company, Organic Reactions, Chapter 6, 1949, pp. 290-300.
Gattermann, L. and Koch, J.A., "New Synthesis of Aromatic Aldehydes", Berichte der Deutschen Chemischen Gesellschaft, 1897, 30, pp. 1622-1624. From J. Chem. Soc., Abstr 72, I, 519-20, 1897. Abstract only translated.

* cited by examiner

*Primary Examiner* — Porfirio Nazario Gonzalez
*Assistant Examiner* — Kofi Adzamli
(74) *Attorney, Agent, or Firm* — James A. Jubinsky

(57) ABSTRACT

The present invention is a process for preparing a 4-alkyl-benzaldehyde (para-alkylbenzaldehyde). An alkylbenzene, solvated in a solvent comprising at least one aliphatic solvent having in the range of 3 to 15 carbons, is reacted with carbon monoxide, in the presence of an aluminum halide and a hydrogen halide acid. Disproportionation is reduced and proportion of para-alkyl-benzaldehyde is increased with respect to other methods.

27 Claims, No Drawings

PRODUCTION OF PARA-PROPYLBENZALDEHYDE

REFERENCE TO RELATED APPLICATIONS

This application is the National Stage of International Patent Appl. No. PCT/US2014/026096 filed on Mar. 13, 2014, which in turn claims the benefit of the priority of commonly-owned U.S. Provisional Patent Appl. No. 61/791,393, filed on Mar. 15, 2013, the disclosure of which is incorporated herein by reference.

TECHNICAL FIELD

The present invention pertains to methods for the production of para-propylbenzaldehyde.

BACKGROUND

In general, the production of para-propylbenzaldehyde has been hampered by low yields and/or requirements that hazardous reactants and reagents be used at high pressures. Processes such as the Duff Formylation (formylation of propylbenzene with hexamine in trifluoroacetic acid to give para-propylbenzaldehyde) result in relatively low yields of the para-isomer. The formylation of an alkylbenzenes with carbon monoxide in the presence of hydrogen chloride and aluminum chloride to give para-propylbenzaldehyde was first reported by Gattermann and Koch in 1897. (Gattermann and Koch, Chemische Berichte, 1897, 30, 1622.) The reaction, known as the "Gattermann-Koch" reaction, has been reviewed by Crounse in Organic Reactions, 1949, 5, 290 and by Olah and Huhn in Friedel-Crafts and Related Reactions, 1964, Vol. 3, Part 2, 1153. Use of the Gattermann-Koch reaction with hydrogen chloride and aluminum trichloride generally gives an increased production of para-product with respect to ortho and meta isomers. Other processes, such as the Gattermann-Koch carbonylation of propylbenzene with carbon monoxide, in this case, in the presence of hydrogen fluoride and boron trifluoride, require the use of hazardous compounds, i.e., hydrogen fluoride and boron trifluoride at high pressures.

Alkylbenzenes have been observed to undergo disproportionation (alkylation and dealkylation) in the presence of aluminum chloride. In the disproportionation reaction, the catalyst causes the transfer of the alkyl substituent of the propylbenzene substrate to another aromatic molecule, such as a molecule of propylbenzene reactant, giving aromatic impurities such as dipropylbenzene and benzene. Tripropylbenzene impurities can also be formed. Formylation product may also undergo disproportionation, giving additional impurity species. These byproduct impurities are generally formed at the expense of the desired formylated para product, thus giving a reduced yield of the desired product. The disproportionation of alkylbenzene in the presence of aluminum chloride is generally known in the art and has been reported by Crounse, J. Am. Chem. Soc., 1949, 71, 1263 and by Baddeley and Kenner, J. Chem. Soc., 1935, 303.

The Gattermann-Koch reaction has been conducted in various aromatic solvents such as benzene, nitrobenzene, chlorobenzene, and halogenated hydrocarbons, or an excess of the aromatic compound to be formylated. U.S. Pat. No. 4,622,429 discloses relatively low yields of formylation product when benzene is used as solvent. U.S. Pat. No. 4,195,040 and German Patent DE403,489 employ chlorobenzene and nitrobenzene, respectively as solvents. Instead of excess aromatic reactant, benzene has been used to some extent in reducing the effects of disproportionation and increasing the yields of alkylbenzaldehyde. In spite of these efforts, a need exists for a Gatterman-Koch-type formylation reaction which reduces the incidence of disproportionation product, but which allows for improved para-product selectivity with respect to current methods.

THE INVENTION

Remarkably, it has been found that the use of aliphatic hydrocarbons as solvents in Gattermann-Koch-type reactions can improve para-isomer yield and dramatically reduce the incidence of disproportionation. Generally, aliphatic hydrocarbon solvents have not been thought to be appropriate as solvents in the Gattermann-Koch formylation because aluminum chloride and hydrochloric acid generally have significantly less solubility in aliphatic hydrocarbons than in aromatic hydrocarbons. However, it has been discovered that when alkylated benzene compounds are carbonylated with carbon monoxide in an aliphatic solvent, in the presence of aluminum chloride and a hydrogen halide, the selectivity of carbonylation favors the formation of the para-isomer to a greater degree than other carbonylation reactions known in the art. Furthermore, the disproportionation (alkyl transfer) reaction is also significantly reduced with respect to other Gattermann-Koch reactions.

Broadly, the present invention is a process for preparing a 4-alkyl benzaldehyde, the process comprising reacting an alkylbenzene, solvated in a solvent comprising at least one aliphatic solvent having in the range of 3 to 15 carbons, with carbon monoxide, in the presence of an aluminum halide and a hydrogen halide acid.

In another embodiment, the present invention is a process for synthesizing a 4-alkyl-benzaldehyde, the process comprising the steps of:

A) adding to a reactor an alkyl benzene, aluminum halide, and at least one aliphatic hydrocarbon solvent having in the range of 3 to 15 carbons;
B) cooling the contents of the reactor to 0 to −50° C.;
C) adding to the reactor an amount of hydrogen halide acid sufficient to charge the reactor to a pressure in the range of about 25 psig to about 200 psig HCl;
D) adding to the reactor an amount of carbon monoxide sufficient to charge the reactor to a pressure in the range of about 200 psig to about 2000 psig; and
E) maintaining a reaction temperature within the reactor at one or more temperatures in the range of about −50° C. to about 20° C.;

thereby synthesizing a 4-alkylbenzaldehyde. In one embodiment, the molar ratio of the hydrogen halide acid to alkylbenzene is at one or more ratios in the range of 1:1 to 20:1.

While it is expected that the benefits of the method are obtained even in the case in which the reaction is not allowed to go to completion, in preferred embodiments the reaction is allowed to proceed until it at least approaches completion, if not until the reaction is complete.

The formylation reaction conducted according to the present invention generally produces the para isomer in surprisingly high yields with respect to the meta isomer, the ortho isomer, and all disproportionation products. Thus, in some embodiments, the invention includes the process above wherein the para product is produced in such high amounts with respect to other isomers and disproportionation products that Gas Chromatography analysis of the reaction mixture after, and optionally, prior to reaction completion indicate that the para isomer is formed in greater than 85 GC area % with respect to all aromatic reaction products (i.e., ortho and meta isomers as well as DNPB and DPBA disproportionation reaction products). The reaction can also give a superior selectivity of para isomer with respect to ortho and meta isomers. In other embodiments, the invention comprises a process as in steps a-d above wherein the reaction within the reactor proceeds until the aluminum chloride is used up and the ortho:meta:para isomer ratio is such that the para-isomer is at least 90 GC Area percent with respect to the combined ortho- and meta- and para-isomers.

DETAILED DESCRIPTION OF THE INVENTION

Surprisingly, it has been found that performing the Gattermann-Koch formylation in aliphatic solvents, or in mixtures of aliphatic and aromatic solvents, rather than only aromatic solvents as has been the practice heretofore, can significantly increase the yield of the para-isomer in the formylation reaction product distribution. Without desiring to be bound by theory, the increased yield is thought to be due to a reduction in the amount of n-alkylbenzene substrate which undergoes disproportionation, as the inventor has discovered that the use of aliphatic solvents has the effect of reducing the incidence of disproportionation such that the formation of multisubstituted disproportionation products, such as, for example DNPB (di-n-propylbenzene) and DPBA (dipropylbenzaldehyde) is dramatically reduced, in some cases to negligible levels. For example, it has been discovered that the use of an aliphatic solvent instead of (or with) an aromatic solvent can reduce the incidence of disproportionation products by upwards of 75 to 95%. The above can be seen by comparing Comparative Examples 1 and 2 with Examples 12 and 13.

The use of aliphatic compounds as solvents causes an unexpectedly efficient suppression of the disproportionation reaction. For instance, as demonstrated by comparing Example 11 with Comparative Example 1, if aliphatic solvents are used, cutting the aromatic reactant proportion roughly in half can reduce the amount of disproportionation products (DNPB) and (DPBA) by over 10-fold. Such a result is even more remarkable in light of the fact that one of skill in the art would expect that the disproportionation reaction would have reached its maximum rate (as a function of aromatic reactant) well before the reactant predominated to the complete exclusion of other solvent species.

Unless otherwise specified, the yields discussed herein of ortho-, meta- and para-products are based upon the amount of consumed n-propylbenzene (NPB). It is known that aluminum chloride is treated as a catalyst in Gatterman-Koch reactions. However, it is also a reaction participant, and is believed to be released at the end of the reaction, when the addition of water is used to give the product and aluminum chloride. Thus, even though aluminum chloride may satisfy the definition of a catalyst, it is a rate limiting reactant as well, and is therefore used in amounts which are typically considered to be in excess of catalytic.

In some embodiments of this invention, the aliphatic hydrocarbon solvent comprises greater than 90 wt % n-alkanes. In further embodiments, the solvent comprises more than 95 wt percent of one or more of the following: propane, n-butane, n-pentane, n-hexane, n-heptane, n-octane, n-nonane, n-decane, n-undecane, n-dodecane, n-tridecane, n-tetradecane, and n-pentadecane.

Furthermore, the inventor has also discovered that the use of aliphatic solvents comprising secondary, tertiary and quaternary aliphatic isomers, such as branched isomers and cyclic isomers, promote the formation of even higher yields of the para product than observed with the use of primary aliphatic isomers. It has been observed that the reduction in di-n-propylbenzene (DNPB) and dipropylbenzaldehyde (DPBA) formed can be such that the ratio of disproportionation products (DNPB and DPBA) to the total of all aromatic products (i.e., DNPB; DPBA; and ortho, meta and para NPBA) is reduced by 40, 50, 60, up to 75 to 95% with respect to the use of n-isomers (compare Examples 3, 4, 5 and 13, with Examples 1, 2 and 12), and in some cases, as much as 90.0-99.5% (i.e., several orders of magnitude) with respect to aromatic solvents (compare Examples 3, 4, 5 and 13 with Comparative Examples 1 and 2). It is shown that the increases in yield of para-product which are observed with the use of branched and/or cyclic aliphatic solvents (even above that demonstrated for non-branched aliphatic solvents) are at the expense of disproportionation. Such a finding is entirely unexpected.

Accordingly, in some embodiments, the aliphatic hydrocarbon solvent comprises greater than 10 wt % branched isomers. In further embodiments, the solvent comprises one or more of the following: butanes, isobutane, pentanes, isopentane, neopentane, hexanes, 2-methylpentane, 3-methylpentane, 2,2-dimethylbutane, 2,3-dimethylbutane, heptanes, 2-methylhexane, 3-methylhexane, 2,2-dimethylpentane, 2,3-dimethylpentane, 2,4-dimethylpentane, octanes, isooctane, 2,2-dimethylhexane, 2,2,3,3-tetramethylbutane, nonanes, decanes, and various commercial petroleum distillates and mixture thereof. Examples of commercially available mixtures include Isopar™, Isopar-C™ (largely isooctane or 2,2,4-trimethylpentane), and Exxsol™.

The enhanced para isomer formation has been shown in the cases of solvents that are typically recognized as aliphatic ring-containing solvents, as well as aliphatic solvents having typically "branched" configurations. As with the branched isomers, it has been observed that the reduction in di-n-propylbenzene (DNPB) and DPBA (dipropylbenzaldehyde) formed can be such that the ratio of disproportionation products (DNPB and DPBA) to the total of all aromatic products (i.e., DNPB; DPBA; and ortho-, meta- and para-NPBA) is reduced by 40, 50, 60, up to 75 to 95% with respect to the use of n-isomers (compare Examples 3, 4, 5 and 13, with Examples 1, 2 and 12), and in some cases, up to 90.0-99.5% (i.e., again, as with branched isomers, several orders of magnitude) with respect to aromatic solvents (compare Examples 3, 4 and 5 and 13 with with Comparative Examples 1 and 2). It is thought that some solvent component having structure in excess of primary structure is required in order to obtain the ultra low disproportionation. In fact, the amount of di-n-propylbenzene (DNPB) of about 1.5%, 1.0% or even less, based upon the weight of the alkyl benzene reactant consumed.

Accordingly, in some embodiments, the aliphatic hydrocarbon solvent comprises greater than 5 wt % cyclic aliphatic isomers. In further embodiments, the solvent comprises one or more of the following: alkyl-substituted cyclopentane, alkyl-substituted cyclohexane, alkyl-substituted cycloheptane, alkyl-substituted cyclooctane, decalin, cyclopentane, cyclohexane, cycloheptane, cyclooctane, methylcyclopentane, methylcyclohexane, dimethylcyclopentane, dimethylcyclohexane and the like. By "alkyl-substituted" is meant that the aliphatic ring bears one or more alkyl substituents. Alkyl-substituted cyclic aliphatic compounds may be mono-, di, tri- or tetra-substituted, and preferred alkyl substituents are methyl, ethyl, isopropyl, n-propyl, isobutyl, tert-butyl, n-butyl, sec-butyl and the like.

The aluminum halide can be aluminum chloride or aluminum bromide. A preferred aluminum halide is aluminum chloride. A convenient molar ratio of alkylbenzene reactant to aluminum chloride is approximately 1:1. Both alkylbenzene and aluminum chloride can be fully utilized. In reality the undesired disproportionation reaction will likely consume some of the alkylbenzene reactant, but the inventive process minimizes such a loss. While an excess of aluminum chloride does not prevent the practitioner from realizing the benefits of the process of the invention, excess solid aluminum chloride reagent could result in handling complications. An excess of aluminum chloride with respect to the alkylbenzene reactant generally does not significantly impact yield based on the consumed alkylbenzene reactant.

In general, in order to facilitate handling during workup, it is somewhat preferred to have a slight excess of alkylbenzene reactant with respect to aluminum chloride to facilitate the complete reaction of the aluminum chloride to give aromatic aldehyde-aluminum chloride complex in liquid form.

In case any unreacted or excess alkylbenzene reactant remains in the product, it can be recycled after isolation and purification of the reaction product.

In general, the benefits of the methods of this invention are obtained even in the case in which the reaction is not allowed to go to completion. In preferred embodiments the reaction is allowed to proceed until it at least approaches completion, if not until the reaction is complete. Step E) is preferably performed until the uptake of carbon dioxide reactant stops or decreases to a negligible level. By complete, it is meant that the uptake of carbon monoxide reactant stops or at least slows to a rate of less than 0.01 mole percent, based upon the number of moles of the limiting reactant, per minute. In preferred embodiments, the aluminum chloride is the limiting reactant. This is possible because aluminum chloride, which is generally classed as a catalyst, is actually temporarily consumed in the formylation reaction. It is ultimately liberated from the reaction product by the addition of water to the reaction mixture to give one molecule of aluminum chloride per molecule of formylated product. In most reaction spaces, charging the carbon monoxide reactant to the required pressure will give amounts well in excess of the aluminum chloride reactant, and thus, the carbon monoxide is not generally a limiting reactant. (However, in some cases, the pressure limit of the reactor may be below the lower limit of the above range, and in such cases, the carbon monoxide may be the limiting reactant.) In other situations, the alkylbenzene reactant may be the limiting reactant. In a another embodiment, CO is fed constantly to maintain pressure in a desired range.

The meaning of the word "solvent," as used herein, should be understood in the following context. Because aluminum chloride participates as a reactant in the formylation reaction of this invention and is liberated in its original form only after the reaction is complete (i.e., by the addition of water to the aromatic reaction product to give, among other things, the aromatic aldehyde and aluminum chloride), it functions as a yield-limiting reactant. In the reaction described herein, the aluminum chloride can be used as a limiting reagent with respect to the aromatic reactant, and thus, at the end of the reaction, it is possible that some amount of aromatic reactant material remains unreacted.

Furthermore, there is no requirement that require that the solvent be 100 percent aliphatic. For example, an aromatic reactant may be reacted in great excess with respect to aluminum chloride. The excess essentially functions as an aromatic solvent, and could instead be one or more of many other aromatic solvents.

Thus, the word "solvent," as used herein, refers to the liquid components which remain unformylated, regardless of whether or not the component is the same compound as the reactant. For example, in some of the experimental runs disclosed herein, n-propylbenzene is used as a reactant and, due to its use in great excess (with respect to aluminum chloride), it serves as a solvent in which formylation takes place. In other examples, the n-propylbenzene reactant is used in only minor excess, with an aliphatic compound such as, for example, MCH (methylcyclohexane) used as the major solvent. In the latter case, the solvent for purposes herein is considered to be the aliphatic compound, as well as the excess n-propylbenzene reactant. The numerical parameters given herein reflect this designation.

The meaning of the word solvent can include a pure compound, such as in the case that the n-alkylbenzene reactant is used in great excess with no other solvents; or in the case that the n-alkylbenzene reactant is not used in excess, and another compound is used in a solvent capacity. The solvent can also be a mixture, combination, or blend of compounds, such as in the experimental runs which include aliphatic compounds in a solvent capacity, as well as excess aromatic compound, such as, for example, starting material.

The amount of aluminum chloride can make a difference in the amount of material considered to be "solvent" in a given reaction. For example, when the n-alkylbenzene reactant is present in stoichiometric excess of the amount of aluminum chloride reactant, the excess is considered for purposes herein to be an aromatic solvent. On the other hand, if aluminum chloride is present in excess of the n-alkylbenzene reactant, all of the n-alkylbenzene reactant will be considered to be solvent, regardless of what other components are present in the reactor.

In general, it has been found that when aliphatic compounds are used in a solvent capacity as indicated herein, the disproportionation reaction of aromatic compounds, including both reactants and solvents, is unexpectedly decreased to very low levels compared to reactions employing aromatic solvents.

The discovery described herein makes it possible to reduce the formation of disproportionation impurities and improve the production of para-n-alkylbenzaldehyde isomer by aluminum chloride mediated formylations by using solvent mixtures, blends or combinations. For example it may be convenient to formylate n-alkylbenzene using an excess of aromatic reactant as a solvent. In such cases, it is not necessary to switch solvents completely in order to realize the benefits of the invention. The aromatic solvent can be augmented with aliphatic solvents as described herein in order to give reduced impurities and increased para-isomer formation. Branched aliphatic solvents and/or cyclic aliphatic solvents can be used to give particularly good efficiencies. In general, the use of mixtures that are in the range of about 90 to about 100 wt % n-isomers can be expected to raise the proportion of para-isomer in the range of from about 75 to about 95%, based upon the proportion of para isomers observed with respect to the same process conducted with aromatic solvents. The use of mixtures that are in the range of about 30 to about 100 wt % branched and/or cyclic alkane can be expected to raise the proportion of para-isomer in the range of from about 90.0 to about 99.5%, based upon the proportion of para isomers observed with respect to the same process conducted with aromatic solvents. Mixtures of branched, cyclic and n-alkanes can be expected to give intermediate effect with respect to para-alkylbenzaldehyde enhancement and disproportionation suppression. In some embodiments, n-alkane solvents, branched aliphatic solvents and/or cyclic aliphatic solvents or mixtures thereof, such as, for example n-hexane, branched hexane isomers, and methylcyclohexane, or combinations thereof are added to aromatic solvents.

In yet other embodiments, the amount of n-solvents, branched solvents and/or cyclic solvents or mixtures thereof added to one or more aromatic solvents is enough such that the proportion of para-alkylbenzaldehyde with respect to the ortho and meta isomers is greater than 90% by GC or NMR analysis.

The n-alkylbenzene reaction substrate can be simply benzene, or methyl, ethyl, n-propyl, n-butyl, n-pentyl, n-hexyl, n-heptyl, n-octyl or even higher order n-alkyl-substituted benzene. It should be noted, that alkyl-substituted benzene substrates other than n-alkyl substituted substrates are expected to show some degree of para-selectivity and disproportionation suppression when used in the process of the present invention. For example, aromatic substrates which are substituted with branched alkyl groups such that the alkyl group attached to the aromatic ring is a primary, secondary, or tertiary alkyl group (such as is the case with isobutylbenzene, sec-butylbenzene, or t-butylbenzene, respectively) can be used.

Hydrohalic acid (hydrogen halide) is a catalyst in Gattermann-Koch reaction and it is not consumed in the reaction. The preferred form of hydrohalic acid is anhydrous gas. The amount of hydrogen chloride can have a significant effect on the reaction rate of this reaction. In one embodiment, the molar ratio of the hydrogen halide to alkylbenzene reactant is from 1:1 to 20:1. A preferred molar ratio of hydrogen halide to alkylbenzene reactant is from 2:1 to 5:1. It has also been found that conducting the reaction at high hydrogen halide pressures and/or relatively low reaction temperature has the effect of favoring the formation of the para isomer. Thus, in some embodiments, in step (C), the amount of hydrogen halide acid is in an amount sufficient to charge the reactor to one or more pressures in the range of about 25 psig to about 200 psig, or in other embodiments, in the range of about 40 psig to about 130 psig. In other embodiments, the amount of hydrogen halide acid is in an amount sufficient to charge the reactor to one or more pressures in the range of about 80 psig to about 120 psig. In other embodiments, the reaction temperature is in the range of about −35° C. to about 20° C., and in other embodiments, in the range of about −35° C. to about 5° C.

Carbon monoxide (CO) is a reactant in the Gattermann-Koch reaction and CO is consumed as the reaction proceeds. Both hydrogen halide (catalyst) and carbon monoxide (reactant) are present in the headspace of the reactor, preferably at a total pressure of greater than about 250 psig, such that reaction proceeds at an appreciable rate to essential completion, if desired. The CO reactant and hydrogen halide may be charged in any order. They may be charged separately, such that the charging of one is concluded before the charging of the other. Alternatively, they may be charged simultaneously. In one embodiment, in step (D), the amount of carbon monoxide is the sufficient to charge the reactor a total pressure of about 300 psig to about 1000 psig. In another embodiment in step (D), the time sufficient for the reaction to proceed to completion is about 4 hours or less.

The pressure in the reactor may decrease as the amount of CO in the reactor headspace is decreased due to the formylation of the alkylbenzene reactant to form alkylbenzaldehyde products. It is permissible to increase the reactor charge of CO, even at a point after the commencement of the reaction. For example, the charge can be increased during the reaction to maintain a relative steady pressure. Alternatively, if the CO content decreases such that the rate of the reaction slows to an excessive degree, the reactor can be recharged with CO in order to increase the rate of reaction.

As mentioned elsewhere herein, it is not necessary to allow the reaction to go to completion in order to realize the benefits of the invention. By "completion" is meant until a yield limiting reactant (the alkylbenzene, carbon monoxide or aluminum chloride, depending upon which is in shortest stoichiometric supply) is used up. For example, the reaction can be stopped, such as by quenching the reaction mixture with water, and the alkylbenzaldehyde products separated out.

The Gattermann-Koch reaction involves three physical forms in the reaction mixture, such as solids (aluminum chloride), liquids (alkylbenzene reactant and aliphatic hydrocarbon solvent), and gases (hydrogen halide and carbon monoxide). In general, the reactants, solvent, and catalysts (alkylbenzene, carbon monoxide, aliphatic hydrocarbons, hydrogen halide, and aluminum chloride) can be charged separately in all possible sequences and combinations. Alternatively, they may be charged simultaneously. In practice, the charging sequence is largely depending on capability of the available equipment and safe handling recommendations. For example, liquids and solids can be charged first if the equipment is incapable of charging liquid and solid under pressure.

The process is conveniently performed in a reactor, such as, for example, an autoclave. In a preferred embodiment, the alkylbenzene reactant, the aliphatic solvent, and the aluminum chloride reactant are charged to an autoclave under anhydrous conditions, such as under a blanket of nitrogen or other inert gas. The temperature at which the charging of the reactor is not critical and it can be performed at room temperature. The reactor is then sealed and its contents agitated, if desired, and the temperature of the reactor is cooled to a temperature in the range of about 20 to about −50° C., and more preferably in the range of about 0 to −30° C. The hydrohalic acid (hydrochloric acid or hydrobromic acid) can then be charged to the reactor to a pressure in the range of from about 25 to about 200 psig, and more preferably in the range of about 40 to about 130 psig. It is preferred that the hydrohalic acid be anhydrous. In a preferred embodiment, the temperature of the reaction is maintained at one or more temperatures below −10° C., such as at approximately −20° C. during the addition of the hydrohalic acid. In one embodiment, the temperature is at least partially controlled by the rate of addition of the hydrohalic acid to the reactor.

The reactor is pressured with CO to a pressure preferably in the range of about 200 to about 2000 psig or up to the pressure limit of the apparatus, and more preferably in the range of about 300 to about 1000 psig.

Once the reactants, solvents and catalysts are charged to the reactor, it can be beneficial to increase the temperature of the reactor to a point at which a controlled consumption of CO is observed. For example, the temperature of the reactor can be slowly raised to a temperature in the range of about −40 to about 20° C., and more preferably in the range of −25 to 0° C. For example, it can be beneficial to maintain the reaction at the foregoing temperatures for times in the range of about 0.5 to about 5 hours. However, the time until CO consumption has slowed can depend upon the size of the batch, and times longer and shorter than the foregoing range may be required. The reaction temperature is maintained in the range of 0 to −35° C. for 30 to 120 minutes. The reaction temperature is dependent of the amount of HCl charged, but it is beneficial to cool the reaction to a temperature in the foregoing ranges regardless of the amount of hydrogen chloride used. Once the consumption of CO had nearly stopped, the reaction temperature can be slowly increased. For example, the reactor temperature can be raised to a temperature in the range of from −50 to about 0° C. at a rate in the range of about 0.05 to about 2 degrees per minute. Final temperatures can be in the range of from 0 to 20° C., for example. When the consumption of CO has abated or the reaction has proceeded to the desired degree, the pressure in the reactor can be released. If desired, the HCl and remaining CO and can be recycled.

The aluminum chloride can be liberated from the n-alkylbenzaldehyde product by quenching the reaction mixture to at least a stoichiometric amount of water to the reaction product. For example The reaction mixture can be contacted with a stoichiometric excess of cold water, preferably at a temperature in the range of about 0 to about 50° C., and preferably with agitation. The organic phase, which contains the alkylbenzaldehyde product can be separated and processed. Common methods which can be used to separate the benzaldehyde reaction product include extraction, distillation, chromatographic methods and the like.

In many cases the yield of para-isomer is greater than 85%, 90%, 95% or even 96% based on the consumed alkylbenzene reactant. In other embodiments, the proportion of para product as compared with ortho and meta products is at least 90%, 95% 97% or even 98%. Non-isolated yields can be measured by quantitative analyses, for example, quantitative chromatographic and NMR methods.

Reported numbers in the accompanied tables in the following examples are in percent based on integration of area under curve by GC analysis. Reported numbers for isomer ratio of o-/m-/p- are normalized to 100 based on GC analysis. Yields reported in the following tables are in percent based on integration of the aldehyde resonances related to an internal standard by NMR analysis.

Comparative Example 1

NPB (n-propylbenzene, 35.0 g), and aluminum chloride (10.0 g) were charged to a 100-mL, Hastelloy C autoclave under nitrogen. The reactor was sealed and set up in the hood. Agitation was set at 500 rpm and the reactor was cooled to 0° C. Anhydrous HCl was slowly added until pressure gauge reached 40 psig. The reactor was pressured with CO to 450 psig and the CO pressure was kept at 300-450 psig throughout the reaction. Reaction temperature was then kept at 0-10° C. for 60 minutes. Pressure was released thru a caustic scrubber slowly. Reaction mixture was transferred to 100 mL/60 mL of icy water/dichloromethane mixture in a quench flask with agitation. The mixture was transferred to the separation funnel. The organic phase was collected and analyzed by GC. Ratio of o-/m-/p-isomer was 13.3:1.2:85.5 by GC. Product mixture contained about 23.8 GC area % of disproportionated products (sum of dipropylbenzene and dipropylbenzaldehyde) based on the consumed n-propylbenzene.

| Compound | Benzene | NPB | DNPB | o-NPBA | m-NPBA | p-NPBA | DPBA | o-/m-/p- |
|---|---|---|---|---|---|---|---|---|
| C. Ex. 1 | n.i. | 67.11 | 3.89 | 3.05 | 0.28 | 21.43 | 4.01 | 12.31/1.13/86.56 |

Comparative Example 2

NPB (35.0 g), aluminum chloride (10.0 g), and methylcyclopentane (0.13 g) were charged to a 100-mL, Hastelloy C autoclave under nitrogen. The reactor was sealed and set up in the hood. Agitation was set at 500 rpm and the reactor was cooled to 10° C. Anhydrous HCl was slowly added until pressure gauge reached 50 psig. The reactor was pressured with CO to 450 psig and the CO pressure was kept at 200-450 psig throughout the reaction. Reaction temperature was gradually increased from 10° C. to ambient for 120 minutes. Pressure was released thru a caustic scrubber slowly. Reaction mixture was quenched icy water and extracted with dichloromethane. The product mixture was collected and analyzed by GC and GC/MS. Ratio of o-/m-/p-isomer was 26.2:1.4:72.4 by GC. Product mixture contained about 60.5 GC area % of disproportionated products (sum of dipropylbenzene and dipropylbenzaldehyde) based on the consumed n-propylbenzene.

| Compound | Benzene | NPB | DNPB | o-NPBA | m-NPBA | p-NPBA | DPBA | o-/m-/p- |
|---|---|---|---|---|---|---|---|---|
| C. Ex. 2 | n.i. | 48.00 | 7.88 | 4.56 | 0.24 | 12.60 | 23.58 | 26.2/1.4/72.4 |

Example 1 n-Pentane (20.0 g), n-propylbenzene (10.0 g), and aluminum chloride (10.0 g) were charged to a 100-mL, Hastelloy C autoclave under nitrogen. The reactor was sealed and set up in the hood. Agitation was set at 500 rpm and the reactor was cooled to 0° C. Anhydrous HCl was slowly added until pressure gauge reached 55 psig. The reactor was pressured with CO to 450 psig and the CO pressure was kept at 350-450 psig throughout the reaction. Temperature was slowly increased to 15° C. for 60 minutes until consumption of CO nearly stopped. Pressure was released thru a caustic scrubber slowly. Reaction mixture was transferred to 50 g of icy water (containing a small amount of conc. HCl) in a quench flask with agitation. The mixture was transferred to the separation funnel. The bottom aqueous phase (58.4 g) was removed. The top organic phase (28.5 g) was collected and analyzed by GC. Ratio of o-/m-/p-isomer was 4.0:1.3:

94.7 by GC. Product mixture contained about 5.6 GC area % of disproportionated products (sum of dipropylbenzene and dipropylbenzaldehyde) based on the consumed n-propylbenzene.

Example 2 n-Heptane (20.0 g), n-propylbenzene (10.0 g), and aluminum chloride (10.0 g) were charged to a 100-mL, Hastelloy C autoclave under nitrogen. The reactor was sealed and set up in the hood. Agitation was set at 500 rpm and the reactor was cooled to 0° C. Anhydrous HCl was slowly added until pressure gauge reached 55 psig. The reactor was pressured with CO to 450 psig and the CO pressure was kept at 350-450 psig throughout the reaction. Temperature was slowly increased to 15° C. for 60 minutes until consumption of CO nearly stopped. Pressure was released thru a caustic scrubber slowly. Reaction mixture was transferred to 50 g of icy water (containing a small amount of conc. HCl) in a quench flask with agitation. The mixture was transferred to the separation funnel. The bottom aqueous phase (59.4 g) was removed. The top organic phase (31.2 g) was collected and analyzed by GC. Ratio of o-/m-/p-isomer was 4.1:1.3:94.6 by GC. Product mixture contained about 6.2 GC area % of disproportionated products (sum of dipropylbenzene and dipropylbenzaldehyde) based on the consumed n-propylbenzene.

Example 3

Hexanes (mixture of isomers, 20.0 g), n-propylbenzene (10.0 g), and aluminum chloride (10.0 g) were charged to a 100-mL, Hastelloy C autoclave under nitrogen. The reactor was sealed and set up in the hood. Agitation was set at 500 rpm and the reactor was cooled to 0° C. Anhydrous HCl was slowly added until pressure gauge reached 55 psig. The reactor was pressured with CO to 450 psig and the CO pressure was kept at 350-450 psig throughout the reaction. Temperature was slowly increased to 20° C. for 60 minutes until consumption of CO nearly stopped. Pressure was released thru a caustic scrubber slowly. Reaction mixture was transferred to 50 g of icy water (containing a small amount of conc. HCl) in a quench flask with agitation. The mixture was transferred to the separation funnel. The bottom aqueous phase (59.7 g) was removed. The top organic phase (29.3 g) was collected and analyzed by GC. Ratio of o-/m-/p-isomer was 3.8:1.5:94.8 by GC. Product mixture contained about 1.4 GC area % of disproportionated products (sum of dipropylbenzene and dipropylbenzaldehyde) based on the consumed n-propylbenzene.

Example 4

Methylcyclohexane (23.0 g), n-propylbenzene (10.0 g), and aluminum chloride (10.0 g) were charged to a 100-mL, Hastelloy C autoclave under nitrogen. The reactor was sealed and set up in the hood. Agitation was set at 500 rpm and the reactor was cooled to 0° C. Anhydrous HBr (16.5 g) was slowly added until pressure gauge reached 55 psig. The reactor was pressured with CO to 500 psig and the CO pressure was kept at 300-500 psig throughout the reaction. Temperature was slowly increased to 5° C. for 20 minutes and then to 15° C. for 40 minutes until consumption of CO nearly stopped. Pressure was released thru a caustic scrubber slowly. Reaction mixture was transferred to 50 g of icy water (containing a small amount of conc. HCl) in a quench flask with agitation. The mixture was transferred to the separation funnel. The bottom aqueous phase (64.3 g) was removed. The top organic phase (33.4 g) was collected and analyzed by GC. Ratio of o-/m-/p-isomer was 3.3:0.9:95.8 by GC. Product mixture contained about 0.5 GC area % of disproportionated products (sum of dipropylbenzene and dipropylbenzaldehyde) based on the consumed n-propylbenzene.

| Compound | Benzene | NPB | DNPB | o-NPBA | m-NPBA | p-NPBA | DPBA | o-/m-/p- |
|---|---|---|---|---|---|---|---|---|
| Ex. 4 | n.i. | 14.92 | <0.1 | 2.80 | 0.75 | 80.27 | 0.30 | 3.3/0.9/95.8 |

Example 5

Methylcyclohexane (23.0 g), n-propylbenzene (10.0 g), and aluminum chloride (10.0 g) were charged to a 100-mL, Hastelloy C autoclave under nitrogen. The reactor was sealed and set up in the hood. Agitation was set at 500 rpm and the reactor was cooled to −15° C. Anhydrous HCl was slowly added until pressure gauge reached 80 psig. The reactor was pressured with CO to 500 psig and the CO pressure was kept at 380-500 psig throughout the reaction. Temperature was slowly increased to −4° C. until moderate CO consumption rate was seen. Reaction mixture was kept at this temperature for 30 minutes and then to 15° C. for 30 minutes until consumption of CO nearly stopped. Pressure was released thru a caustic scrubber slowly. Reaction mixture was transferred to 50 g of icy water (containing a small amount of conc. HCl) in a quench flask with agitation. The mixture was transferred to the separation funnel. The bottom aqueous phase (59.0 g) was removed. The top organic phase (34.8 g) was collected and analyzed by GC. Ratio of o-/m-/p-isomer was 2.4:0.7:96.9 by GC. Product mixture contained about 0.5 GC area % of disproportionated products (sum of benzene, dipropylbenzene, and dipropylbenzaldehyde) based on the consumed n-propylbenzene.

| Compound | Benzene | NPB | DNPB | o-NPBA | m-NPBA | p-NPBA | DPBA | o-/m-/p- |
|---|---|---|---|---|---|---|---|---|
| Ex. 1 | n.i. | 14.01 | 0.74 | 3.19 | 1.06 | 75.93 | 4.11 | 4.0/1.3/94.7 |
| Ex. 2 | n.i. | 15.09 | 1.09 | 3.23 | 1.07 | 74.88 | 4.17 | 4.1/1.3/94.6 |
| Ex. 3 | n.i. | 19.70 | 0.21 | 2.95 | 1.15 | 74.27 | 0.95 | 3.8/1.5/94.8 |

| Compound | Benzene | NPB | DNPB | o-NPBA | m-NPBA | p-NPBA | DPBA | o-/m-/p- |
|---|---|---|---|---|---|---|---|---|
| Ex. 5 | 0.22 | 13.92 | 0.04 | 2.02 | 0.62 | 82.10 | 0.15 | 2.4/0.7/96.9 |

Example 6

Hexanes (mixture of isomers, 20.0 g), n-propylbenzene (10.0 g), and aluminum chloride (10.0 g) were charged to a 100-mL, Hastelloy C autoclave under nitrogen. The reactor was sealed and set up in the hood. Agitation was set at 500 rpm and the reactor was cooled to −15° C. Anhydrous HCl was slowly added until pressure gauge reached 80 psig. The reactor was pressured with CO to 500 psig and the CO pressure was kept at 380-500 psig throughout the reaction. Temperature was slowly increased to −3° C. until moderate CO consumption rate was seen. Reaction mixture was kept at this temperature for 20 minutes and then to 18° C. for 40 minutes until consumption of CO nearly stopped. Pressure was released thru a caustic scrubber slowly. Reaction mixture was transferred to 50 g of icy water (containing a small amount of conc. HCl) in a quench flask with agitation. The mixture was transferred to the separation funnel. The bottom aqueous phase (59.8 g) was removed. The top organic phase (29.8 g) was collected and analyzed by GC and quantitative NMR. Ratio of o-/m-/p-isomer was 2.6:0.7:96.8 by GC. Product mixture contained about 1.1 GC area % of disproportionated products (sum of benzene, dipropylbenzene, and dipropylbenzaldehyde) based on the consumed n-propylbenzene. Yields (not isolated) of o-/m-/p-isomer were 2.06%, 0.53%, and 93.1%, respectively by quantitative NMR analysis of organic phase.

| Compound | Benzene | NPB | DNPB | o-NPBA | m-NPBA | p-NPBA | DPBA | o-/m-/p- |
|---|---|---|---|---|---|---|---|---|
| Ex. 6 | 0.56 | 11.48 | 0.25 | 2.20 | 0.57 | 83.39 | 0.14 | 2.6/0.7/96.8 |

Example 7

Hexanes (mixture of isomers, 16.0 g), n-propylbenzene (20.0 g), and aluminum chloride (20.0 g) were charged to a 100-mL, Hastelloy C autoclave under nitrogen. The reactor was sealed and set up in the hood. Agitation was set at 500 rpm and the reactor was cooled to −25° C. Anhydrous HCl was slowly added until pressure gauge reached 120 psig. The reactor was pressured with CO to 500 psig and the CO pressure was kept at 400-500 psig throughout the reaction. Temperature was slowly increased to −20° C. until moderate CO consumption rate was seen. Reaction mixture was kept at this temperature for 30 minutes and then to 10° C. for 30 minutes until consumption of CO nearly stopped. Pressure was released thru a caustic scrubber slowly. Reaction mixture was transferred to 60 g of icy water (containing a small amount of conc. HCl) in a quench flask with agitation. The mixture was transferred to the separation funnel. The bottom aqueous phase (78.5 g) was removed and the organic phase was washed with water (20.0 g). The product mixture (44.0 g) was collected and analyzed by GC and quantitative NMR. Ratio of o-/m-/p-isomer was 1.78:0.35:97.87 by GC. Product mixture contained about 0.5 GC area % of disproportionated products (sum of benzene, dipropylbenzene, and dipropylbenzaldehyde) based on the consumed n-propylbenzene. Yields (not isolated) of o-/m-/p-isomer were 1.57%, 0.29%, and 92.9%, respectively by quantitative NMR analysis of organic phase.

| Compound | Benzene | NPB | DNPB | o-NPBA | m-NPBA | p-NPBA | DPBA | o-/m-/p- |
|---|---|---|---|---|---|---|---|---|
| Ex. 7 | 0.3 | 11.59 | 0.09 | 1.55 | 0.31 | 85.44 | 0.09 | 1.78/0.35/97.87 |

Examples 8-10

Hexanes (isomers of hexanes, 48.0 g), n-propylbenzene (60.0 g), and aluminum chloride (60.0 g) were charged to a 300-mL, Hastelloy C autoclave under nitrogen. Note: Anhydrous system needed. The reactor was sealed and set up in the hood. Agitation was set at 600 rpm and the reactor was cooled to −25° C. Anhydrous HCl was slowly added until pressure gauge reached 85 psig. Note: Exothermic. The reactor was pressured with CO to 450 psig and the CO pressure was kept at 400-450 psig throughout the reaction. Temperature was slowly increased to −20° C. until moderate CO consumption rate was seen. Reaction temperature was then kept at −20° C. for 60 minutes. Note: Reaction temperature is dependent of the amount of HCl charged. Reaction temperature was slowly increased to 13° C. over 65 minutes after consumption of CO nearly stopped. Pressure was released thru a caustic scrubber slowly. Reaction mixture was transferred to 180 g of icy water (containing 2 mL of conc. HCl) in a quench flask with agitation. Note: exothermic. Temperature was about 45-50° C. for 20 minutes. The mixture was transferred to the separation funnel. Reactor and flask were washed with 10 mL of hexanes to the separation funnel. The bottom aqueous phase (244 g) was removed. The top organic phase was washed with 60 mL of water. The organic phase (121.5 g) was collected and analyzed by GC and quantitative NMR. Ratio of o-/m-/p-isomer by GC and yields (not isolated) of o-/m-/p-isomer by quantitative NMR analysis of organic phase are given in the table below.

| Compound | Benzene | NPB | DNPB | o-NPBA | m-NPBA | p-NPBA | DPBA | o-/m-/p- |
|---|---|---|---|---|---|---|---|---|
| Ex. 8 | 0.34 | 11.19 | 0.08 | 1.78 | 0.38 | 85.78 | 0.10 | 2.03/0.43/97.55 |
| Ex. 9 | 0.33 | 11.42 | 0.09 | 1.74 | 0.35 | 85.29 | 0.07 | 1.99/0.40/97.61 |
| Ex. 10 | 0.33 | 10.69 | 0.15 | 1.84 | 0.37 | 85.93 | 0.12 | 2.08/0.42/97.49 |

| % Yield by quantitative NMR based on consumed NPB ||||
|---|---|---|---|---|
| Compound | o-NPBA | m-NPBA | p-NPBA | Normalized o-/m-/p- |
| Ex. 8 | 2.54 | 0.64 | 96.4 | 2.6/0.6/96.8 |
| Ex. 9 | 1.77 | 0.55 | 94.2 | 1.8/0.6/97.6 |
| Ex. 10 | 1.78 | 0.45 | 93.9 | 1.9/0.5/97.7 |

Reported numbers in the accompanying tables in the following examples are in percent based on integration of area under curve by GC analysis. Reported numbers of isomer ratio of o-/m-/p- are normalized to 100 based on GC analysis.

GC Conditions:
GC: HP5890 Series II, FID
Integrator: HP3396 Series II
Reported numbers are area % by GC analysis.
Column: J&W Scientific, Cat#1255032, DB-5, 30 m × 0.53 mm × 1.5 um
Oven temp: 70 C. (2 min), 15 C./min, 250 C., 10 C./min, 280 C. (10 min)

| Compound R.T. (min) MW | Benzene | NPB 4.32 120 | DNPB 7.56 162 | o-NPBA 7.73 148 | m-NPBA 7.95 148 | p-NPBA 8.16 148 | DPBA 10.54 190 | Normalized o-/m-/p- |
|---|---|---|---|---|---|---|---|---|
| C. Ex. 1 | n.i. | 67.11 | 3.89 | 3.05 | 0.28 | 21.43 | 4.01 | 12.31/1.13/86.56 |
| C. Ex. 2 | n.i. | 48.00 | 7.88 | 4.56 | 0.24 | 12.60 | 23.58 | |
| Ex. 1 | n.i. | 14.01 | 0.74 | 3.19 | 1.06 | 75.93 | 4.11 | 3.98/1.33/94.69 |
| Ex. 2 | n.i. | 15.09 | 1.09 | 3.23 | 1.07 | 74.88 | 4.17 | 4.08/1.34/94.57 |
| Ex. 3 | n.i. | 19.70 | 0.21 | 2.95 | 1.15 | 74.27 | 0.95 | 3.77/1.47/94.77 |
| Ex. 4 | n.i. | 14.92 | <0.1 | 2.80 | 0.75 | 80.27 | 0.30 | 3.34/0.89/95.77 |
| Ex. 5 | n.i. | 14.48 | <0.1 | 2.05 | 0.58 | 82.48 | 0.14 | 2.40/0.68/96.91 |
| Ex. 6 | n.i. | 11.70 | 0.25 | 2.22 | 0.57 | 83.98 | 0.14 | 2.56/0.66/96.78 |
| Ex. 11 | n.i. | 56.11 | 0.27 | 1.54 | 0.66 | 39.64 | 0.50 | 3.68/1.58/94.74 |
| Ex. 12 | n.i. | 53.00 | 0.90 | 1.98 | 0.44 | 41.91 | 1.22 | 4.47/0.99/94.54 |
| Ex. 13 | n.i. | 21.33 | <0.1 | 2.84 | 1.17 | 73.32 | 0.57 | 3.68/1.51/94.81 |
| Ex. 14 | n.i. | 19.78 | 2.57 | 2.96 | 0.99 | 66.39 | 4.44 | 4.20/1.41/94.38 |
| Ex. 15 | n.i. | 99.58 | | | | | | No reaction |
| Ex. 16 | n.i. | 10.21 | 0.45 | 2.39 | 0.55 | 85.10 | 0.17 | 2.72/0.63/96.65 |

GC Conditions:
Column: J&W Scientific, Cat#1255032, DB-5, 30 m × 0.53 mm × 1.5 um
Oven temp: 40 C. (2 min), 15 C./min, 250 C., 10 C./min, 280 C. (9 min)

| Compound R.T. (min) | Benzene 2.19 | NPB 6.39 | DNPB 9.62 | o-NPBA 9.77 | m-NPBA 9.99 | p-NPBA 10.22 | DPBA 12.55 | o-/m-/p- |
|---|---|---|---|---|---|---|---|---|
| Ex. 5 | 0.22 | 13.92 | 0.04 | 2.02 | 0.62 | 82.10 | 0.15 | 2.38/0.73/96.89 |
| Ex. 6 | 0.56 | 11.48 | 0.25 | 2.20 | 0.57 | 83.39 | 0.14 | 2.56/0.66/96.78 |
| Ex. 7 | 0.3 | 11.59 | 0.09 | 1.55 | 0.31 | 85.44 | 0.09 | 1.78/0.35/97.87 |
| Ex. 8 | 0.34 | 11.19 | 0.08 | 1.78 | 0.38 | 85.78 | 0.10 | 2.03/0.43/97.55 |
| Ex. 9 | 0.33 | 11.42 | 0.09 | 1.74 | 0.35 | 85.29 | 0.07 | 1.99/0.40/97.61 |
| Ex. 10 | 0.33 | 10.69 | 0.15 | 1.84 | 0.37 | 85.93 | 0.12 | 2.08/0.42/97.49 |
| Ex. 16 | 0.67 | 10.00 | 0.45 | 2.35 | 0.55 | 84.37 | 0.17 | 2.70/0.63/96.68 |
| Ex. 17 | 6.77 | 11.83 | 6.35 | 1.82 | 0.25 | 50.63 | 0.12 | 3.46/0.47/96.07 |
| Ex. 18 | 0.53 | 11.68 | 0.41 | 1.39 | 0.22 | 84.43 | | 1.62/0.26/98.13 |
| Ex. 19 | 0.34 | 11.47 | 0.10 | 1.59 | 0.36 | 85.18 | 0.05 | 1.82/0.41/97.77 |
| Ex. 20 | 0.32 | 11.21 | 0.07 | 1.67 | 0.37 | 85.77 | 0.07 | 1.90/0.43/97.67 |
| Ex. 21 | 0.4 | 11.59 | 0.18 | 1.70 | 0.35 | 85.25 | 0.09 | 1.95/0.40/97.65 |
| Ex. 22 | 2.65 | 16.39 | 4.09 | 1.74 | 0.31 | 73.45 | 0.06 | 2.31/0.41/97.28 |
| Ex. 23 | 1.36 | 13.29 | 1.29 | 2.35 | 0.53 | 79.20 | 0.72 | 2.86/0.65/96.49 |

Yields reported in the following tables are in percent based on integration of the aldehyde resonances related to an internal standard by NMR analysis.

| % Yield by quantitative NMR based on consumed NPB ||||||
|---|---|---|---|---|---|
| Run | o-NPBA | m-NPBA | p-NPBA | Normalized o-/m-/p- | Reaction Conditions |
| C. Ex. 1 | | | | | 35 g NPB, 10 g AlCl3, 40 psi HCl, CO, 5 C. |
| C. Ex. 2 | | | | | 35 g NPB, 0.13 g MCP, 10 g AlCl3, 50 psi HCl, CO, RT |
| Ex. 1 | | | | | 10 g NPB, 20 g n-C5, 10 g AlCl3, 50 psi HCl, CO, 14 C. |
| Ex. 2 | | | | | 10 g NPB, 20 g n-C7, 10 g AlCl3, 55 psi HCl, CO, 14 C. |

% Yield by quantitative NMR based on consumed NPB

| Run | o-NPBA | m-NPBA | p-NPBA | Normalized o-/m-/p- | Reaction Conditions |
|---|---|---|---|---|---|
| Ex. 3 | | | | | 10 g NPB, 20 g C6's, 10 g AlCl3, 55 psi HCl, CO, 18 C. |
| Ex. 4 | | | | | 10 g NPB, 23 g MCH, 10 g AlCl3, 60 psi HBr, CO, 5 C. |
| Ex. 5 | 2.27 | 0.70 | 90.9 | 2.4/0.7/96.8 | 10 g NPB, 23 g MCH, 10 g AlCl3, 80 psi HCl, CO, −3 C. |
| Ex. 6 | 2.06 | 0.53 | 93.1 | 2.2/0.6/97.3 | 10 g NPB, 20 g C6's, 10 g AlCl3, 80 psi HCl, CO, −3 C. |
| Ex. 7 | 1.57 | 0.29 | 92.9 | 1.7/0.3/98.0 | 20 g NPB, 16 g C6's, 20 g AlCl3, 120 psi HCl, CO, −22 C. |
| Ex. 8 | 2.54 | 0.64 | 96.4 | 2.6/0.6/96.8 | 60 g NPB, 48 g C6's, 60 g AlCl3, 85 psi HCl, 450 psi CO, −19 C. |
| Ex. 9 | 1.77 | 0.55 | 94.2 | 1.8/0.6/97.6 | 60 g NPB, 48 g C6's, 60 g AlCl3, 85 psi HCl, 450 psi CO, −19 C. |
| Ex. 10 | 1.78 | 0.45 | 93.9 | 1.9/0.5/97.7 | 60 g NPB, 48 g C6's, 60 g AlCl3, 85 psi HCl, 450 psi CO, −19 C. |
| Ex. 11 | | | | | 19 g NPB, 17 g MCH, 10 g AlCl3, 40 psi HCl, CO, 16 C. |
| Ex. 12 | | | | | 19 g NPB, 13.8 g n-C5, 10 g AlCl3, 60 psi HCl, CO, 0 C. |
| Ex. 13 | | | | | 10 g NPB, 23.8 g MCH, 10 g AlCl3, 50 psi HCl, CO, 17 C. |
| Ex. 14 | | | | | 10 g NPB, 23 g MCH, 10 g AlCl3, 55 psi HCl, low CO, 20 C. |
| Ex. 15 | | | | | 30 g NPB, 140 psi BF3, 20 psi HCl, CO, 24 C. |
| Ex. 16 | 2.2 | 0.5 | 93.9 | 2.3/0.5/97.2 | 20 g NPB, 15.7 g C6's, 20 g AlCl3, 80 psi HCl, CO, −9 C. |
| Ex. 17 | | | | | 20 g NPB, 15.7 g C6's, 20 g AlCl3, 180 psi HCl, CO, −25 C. |
| Ex. 18 | 1.02 | 0.16 | 82.1 | 1.2/0.2/98.6 | 20 g NPB, 16 g C6's, 20 g AlCl3, 130 psi HCl, CO, −35 C. |
| Ex. 19 | 1.65 | 0.51 | 93.7 | 1.7/0.5/97.7 | 15 g NPB, 15 g C6's, 15 g AlCl3, 100 psi HCl, CO, −22 C. |
| Ex. 20 | 1.71 | 0.57 | 94.3 | 1.8/0.6/97.6 | 15 g NPB, 12 g C6's, 15 g AlCl3, 85 psi HCl, 450 psi CO, −17 C. |
| Ex. 21 | 1.69 | 0.36 | 94.9 | 1.7/0.4/97.9 | 15 g NPB, 12 g C6's, 15 g AlCl3, 85 psi HCl, 250 psi CO, −17 C. |
| Ex. 22 | 1.58 | 0.55 | 80.2 | 1.9/0.7/97.4 | 15 g NPB, 12 g C6's, 15 g AlCl3, 85 psi HCl, 150 psi CO, −17 C. |
| Ex. 23 | 2.19 | 0.58 | 87.1 | 2.4/0.6/96.9 | 60 g NPB, 48 g C6's, 60 g AlCl3, 75 psi HCl, CO, −9 C. |

It is to be understood that the reactants and components referred to by chemical name or formula anywhere in this document, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical operation or reaction or in forming a mixture to be used in conducting a desired operation or reaction. Also, even though an embodiment may refer to substances, components and/or ingredients in the present tense ("is comprised of", "comprises", "is", etc.), the reference is to the substance, component or ingredient as it existed at the time just before it was first contacted, blended or mixed with one or more other substances, components and/or ingredients in accordance with the present disclosure.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

This invention is susceptible to considerable variation within the spirit and scope of the appended claims.

The invention claimed is:

1. A process comprising:
A) adding to a reactor an alkylbenzene, aluminum halide, and at least one aliphatic hydrocarbon solvent having in a range of 3 to 15 carbons;
B) cooling contents of the reactor to one or more temperatures in a range of 0 to −50° C.;
C) adding to the reactor an amount of hydrogen halide acid sufficient to charge the reactor to a pressure in a range of about 25 psig to about 200 psig;
D) adding to the reactor an amount of carbon monoxide sufficient to charge the reactor to a pressure in a range of about 200 psig to about 2000 psig; and
E) maintaining a reaction temperature at one or more temperatures in a range of about −50° C. to about 20° C.;
thereby synthesizing a 4-alkylbenzaldehyde.

2. A process as in claim 1 wherein a molar ratio of the hydrogen halide acid to the alkylbenzene is in a range of 1:1 to 20:1.

3. A process as in claim 1 wherein Gas Chromatography analysis of reaction mixture after, and optionally, prior to reaction completion indicate that the 4-alkylbenzaldehyde is formed in greater than 85 area % GC based on an amount of alkylbenzene consumed.

4. A process as in claim 1 wherein step E) proceeds until the aluminum chloride is used up and an ortho:meta:para isomer ratio is such that the para-isomer is at least 90 percent by quantitative NMR with respect to combined ortho- and meta- and para-isomers.

5. The process of claim 1, wherein the aliphatic hydrocarbon solvent comprises greater than 90 wt % n-isomers.

6. The process as in claim 5 wherein the aliphatic hydrocarbon solvent comprises one or more of the following: propane, n-butane, n-pentane, n-hexane, n-heptane, n-octane, n-nonane, n-decane, n-undecane, n-dodecane.

7. The process of claim 1 wherein the aliphatic hydrocarbon solvent comprises greater than 10 wt % branched isomers.

8. The process of claim 7 wherein the branched isomers comprise one or more of the following: butanes, isobutane, pentanes, isopentane, neopentane, hexanes, 2-methylpentane, 3-methylpentane, 2,2-dimethylbutane, 2,3-dimethylbutane, heptanes, 2-methylhexane, 3-methylhexane, 2,2-dimethylpentane, 2,3-dimethylpentane, 2,4-dimethylpentane, octanes, isooctane, 2,2-dimethylhexane, 2,2,3,3-tetramethylbutane, nonanes, decanes, and petroleum distillates and mixtures thereof.

9. The process of claim 1 wherein the aliphatic hydrocarbon solvent comprises greater than 5 wt % cyclic aliphatic isomers.

10. The process of claim 9 wherein the cyclic aliphatic isomers comprise one or more of the following: alkyl-substituted cyclopentane, alkyl-substituted cyclohexane, alkyl-substituted cycloheptane, alkyl-substituted cyclooctane, decalin, cyclopentane, cyclohexane, cycloheptane, cyclooctane, methylcyclopentane, methylcyclohexane, dimethylcyclopentane, and dimethylcyclohexane.

11. The process of claim 1, wherein, in step (C), an amount of hydrogen halide acid is the amount sufficient to charge the reactor to one or more pressures in a range of about 40 psi to about 130 psi.

12. The process of claim 11, wherein the pressure is from about 80 psig to about 120 psig.

13. The process of claim 1, wherein, in step (D), an amount of carbon monoxide is the amount sufficient to charge the reactor to a total pressure in a range of about 300 psig to about 1000 psig.

14. The process of claim 1, wherein, in step (E), a time sufficient to reach completion is about 4 hours or less.

15. The process of claim 1, wherein a formylated product comprises at least 85% yield by quantitative NMR of 4-propylbenzaldehyde.

16. The process of claim 15, wherein the formylated product comprises at least 90% yield by quantitative NMR of 4-propylbenzaldehyde.

17. The process of claim 1, wherein the reaction temperature is from about −35° C. to about 20° C.

18. The process of claim 17, wherein the reaction temperature is from about −35° C. to about 5° C.

19. The process of claim 1, further comprising a disproportionation product comprising an amount of di-n-propylbenzene (DNPB) of about 1.5% or less.

20. The process of claim 1, further comprising a disproportionation product comprising an amount of dipropylbenzaldehyde (DPBA) of about 1.0% or less.

21. The process of claim 1, wherein a para-isomer is 4-propylbenzaldehyde.

22. The process of claim 1, wherein, in step (E), a para-isomer comprises at least 90 percent of combined ortho, meta, and para isomers.

23. The process of claim 22, wherein, in step (E), the para-isomer comprises at least 97 percent of combined ortho, meta, and para isomers.

24. The process of claim 1, further comprising separating the 4-alkylbenzaldehyde product.

25. The process of claim 24, wherein the separating comprises extraction, distillation, chromatograph, or combinations thereof.

26. The process of claim 1, wherein the hydrogen halide acid is hydrogen chloride or hydrogen bromide.

27. The process of claim 1, wherein the aluminum halide acid is aluminum chloride or aluminum bromide.

* * * * *